United States Patent [19]

Johnson

[11] Patent Number: 5,487,313
[45] Date of Patent: Jan. 30, 1996

[54] FLUID-LOCK FIXED-VOLUME INJECTOR

[75] Inventor: Paul H. Johnson, Oakland, Calif.

[73] Assignee: Microsensor Technology, Inc., Fremont, Calif.

[21] Appl. No.: 158,978

[22] Filed: Nov. 30, 1993

[51] Int. Cl.$^6$ .................... G01N 30/00; G01N 1/00
[52] U.S. Cl. .................. 73/863.71; 73/23.42; 73/864.83
[58] Field of Search ................. 73/23.22, 23.35, 73/23.41, 23.42, 864.81, 864.83, 863.71

[56] References Cited

U.S. PATENT DOCUMENTS

| | | | |
|---|---|---|---|
| 2,841,005 | 7/1958 | Coggeshall | 73/864.86 |
| 2,964,938 | 12/1960 | Fuller | 73/863.71 |
| 3,372,573 | 3/1968 | Sanford et al. | 73/23.42 |
| 3,431,783 | 3/1969 | Radgens | 73/864.86 |
| 3,559,703 | 2/1971 | Maul et al. | 73/864.86 |
| 4,036,062 | 7/1977 | Cruzan | 73/864.83 |
| 4,173,145 | 11/1979 | Durbin | 73/864.83 |
| 4,353,243 | 10/1982 | Martin | 73/23.42 |
| 4,474,889 | 10/1984 | Terry et al. | 422/89 |
| 4,800,761 | 1/1989 | Spencer | 73/863.71 |
| 4,883,505 | 11/1989 | Lucero | 73/864.81 |
| 4,980,130 | 12/1990 | Metzgen et al. | 73/863.71 |
| 5,205,845 | 4/1993 | Sacks et al. | 73/23.42 |
| 5,209,102 | 5/1993 | Wang et al. | 73/864.81 |

OTHER PUBLICATIONS

Brian Pearce et al., "Sample Injection Port for High Pressure Chromatography", in Analytical Chemistry, vol. 44, No. 6, May 1972, pp. 1107–1109.

Valco Product Literature, date unknown.

Stephen C. Terry, et al.; "A Gas Chromatographic Air Analyzer Fabricated on a Silicon Wafer"; *IEEE Transactions on Electron Devices*; vol. ED–26, No. 12, Dec. 1979.

Photovac International, "10Splus Digital Gas Chromatograph", Part No. 380200 Rev. B; Copyright 1991; Index and Chapters 10 and 11.

G. Lee, et al.; "Recent developments in high speed gas chromatography"; *American Library*; Feb. 1989.

*Primary Examiner*—Richard Chilcot
*Assistant Examiner*—George Dombroske
*Attorney, Agent, or Firm*—Skjerven, Morrill, MacPherson, Franklin & Friel; Norman R. Klivans; Emily M. Haliday

[57] ABSTRACT

An automated micro-valve assembly injects a fixed fluid volume fluid into a destination stream. The fluid to be injected (inject fluid) is conducted into a chamber. Flow of inject fluid out of the chamber is prevented by sealing the ends of the chamber using valves or by application of pressure. A fixed volume of inject fluid is injected into the destination stream by pressurizing the inject fluid in the chamber and opening an inject valve which connects the chamber to the destination stream. The pressurization of the inject fluid in the chamber above the destination stream pressure is effected by a T-valve which controls the flow of a purge fluid into the chamber. The purge fluid emitted by the T-valve flows toward the inject valve, forming a fluid-lock which establishes the fixed-volume to be injected. During the injection, the inject fluid is driven by the purge fluid pressure to flow through the inject valve into a destination passage which communicates with the destination stream. The inject fluid in the section of chamber between the T-valve orifice and the inject valve orifice is injected, as the purge fluid emitted at the T-valve displaces the inject fluid from that section of the chamber.

32 Claims, 7 Drawing Sheets

FLUID-LOCK FIXED-VOLUME INJECTOR

BACKGROUND OF THE INVENTION

1. Field of the Invention

This invention relates to an injector to introduce a predetermined amount of fluid into or onto a stream of liquid, solid, or gas, and more particularly to a microvalve injector to introduce a fixed volume of fluid into a destination stream.

2. Description of the Prior Art

The need to add a predetermined amount of a fluid into another material is common. Automated methods to add a predetermined amount of fluid to another material are also common. The method of adding a small amount of a fluid to a destination stream is exemplified by the injector apparatus used in a gas chromatograph.

Gas chromatographs are well known for analysis of chemical mixtures, separation of gases and process measurement and control. A gas chromatograph includes three main components: an analytical column which physically separates the components of a sample mixture, a detector to sense the individual components after separation, and an injector to introduce an amount of the sample into the analytical column for separation. For quantitative analysis, the injector must introduce a controlled amount of sample into the analytical column. The most common injection techniques for gas chromatography are by syringe and by sample loop. A fixed-volume of sample is injected into the analytical column using a sample loop injector.

The conventional well known sample loop injector includes a two-position multiport rotary valve. The sample loop is filled with the sample while a carrier gas flows to the analytical column through channels in the valve. When the valve rotor is turned to move the valve into the second position, the arrangement of valve channels is re-configured, and the sample loop becomes part of the channeling that conducts the carrier gas through the valve to the analytical column. In the second position, the carrier gas flows through the sample loop and the sample is swept from the sample loop and flows in the carrier gas stream to the analytical column. If the sample loop is "internal", then the multiport rotary valve has four ports. If the sample loop is "external", then the multiport rotary valve has six ports. Rotary valves are difficult to miniaturize. Relatively large dead volumes and slow switching times limit the performance of rotary sample valves. In addition, rotary valves are limited in the number of cycles before they wear out due to friction at the seal interface.

In the 10S series gas chromatograph manufactured by Photovac International, four solenoid valves isolate the sample loop during filling with sample and insert the sample loop into the carrier gas stream to the analytical column during sample injection.

U.S. Pat. No. 4,474,889, entitled "Miniature Gas Chromatograph Apparatus" issued on Oct. 2, 1984, and incorporated by reference herein, commonly owned with the present application, describes a sample injection scheme which utilizes a miniaturized injector. In this "timed-injection" scheme, the amount of injected sample depends on the period of time that the inject valve is open. However, the amount of sample that flows into the analytical column during a particular injection time decreases undesirably as the sample viscosity increases. Therefore, the reported response (peak area) of the associated gas chromatograph for a particular analyte decreases as the sample viscosity increases.

There is a need therefore for a fixed-volume sample injector without the drawbacks of a rotary valve sample loop, which can be easily miniaturized, and which injects the same volume of sample despite variations in sample viscosity.

SUMMARY OF THE INVENTION

In accordance with the present invention, an injector assembly to inject a fixed-volume of a fluid sample into a destination stream includes a sample chamber having a sample valve at one end to connect the sample chamber to a sample source, a portion of the sample chamber defining the fixed-volume, elements for introducing the sample into the sample chamber and for trapping the sample therein, a T-valve connected between one end of the fixed-volume portion of the sample chamber and a purge fluid source for controlling the flow of purge fluid into the sample chamber, and an inject valve connected to the other end of the fixed-volume portion of the sample chamber for controlling the flow of sample from the sample chamber to the destination stream. During sample injection, the purge fluid flows through the T-valve into the sample chamber and forces the sample in the fixed-volume portion of the sample chamber through the inject valve into the destination stream. The purge fluid entering the sample chamber forms a "fluid-lock" that segregates the sample in the sample chamber into two parts: the fixed-volume part which flows into the destination stream, and the remainder which does not flow into the destination stream.

The injector device arrangement of valves and the principle of operation disclosed herein is distinct from that of the prior art devices. For example, in one embodiment the present injector device uses pressure to force the sample into the analytical column through a valve orifice; whereas in the case of the Photovac sample loop (and the conventional sample loop using a rotary valve), a reconfiguration of valves causes the carrier gas stream to flow through the sample loop, thereby transporting the sample into the analytical column. A two-event process occurs in the case of the rotary valve sample loop: sample loop filling, then sample injection/analysis. A three-event process occurs in the present injector device sample chamber filling, a brief sample injection event, then sample analysis. The sample chamber in accordance with the invention is isolated from the analytical column (except during the sample injection event); whereas in the rotary valve and the Photovac sample loop injectors, the carrier gas to the analytical column passes through the sample loop during sample injection and sample analysis.

A device in accordance with the invention is more easily miniaturized than is the prior art rotary valve sample loop. Miniaturization of the injector facilitates high-speed chromatographic analysis, which is highly desirable.

In some embodiments of the present invention, a injector purge sequence clears the fluid pathways of undesirable fluids prior to putting the apparatus into service, or as part of a "warm-up" procedure. This injector purge sequence involves opening certain valves in a sequence in order to allow the sample fluid, the purge fluid, or the destination stream to flow and purge undesirable fluids from the injector. For example, this is accomplished by opening the purge valve for a particular time period to allow purge fluid to flow through the purge fluid pathways to a vent.

The injector assembly in accordance with the present invention is usable in a gas chromatograph; then the "destination stream" is the carrier gas stream to the analytical column. The sample may be gas or liquid (fluid) or a combination thereof, and the destination stream may be fluid or solid. The sample is drawn into the sample chamber by the action of a pump, or flows into the sample chamber under its own pressure.

In one embodiment, a valve is provided at each end of the sample chamber for introducing the sample from the sample source into the sample chamber and trapping the sample in the sample chamber.

In another embodiment, the sample chamber is sealed at one end by a valve, and at the other end by the application of pressure (a pressure source such as a pump) to trap the sample in the sample chamber. The pressure to trap the sample is applied using a pressurization fluid similar to the sample, or using the purge fluid (or other appropriate fluid). When the apparatus is used as an injector in a gas chromatograph, carrier gas can be used as both the pressurization fluid and the purge fluid.

For high accuracy analyses, the sample temperature in one embodiment is thermostatically-controlled, because the expansion or contraction of the sample fluid with variation in sample temperature affects the amount of sample trapped in the fixed-volume portion of the sample chamber. For example, in gas chromatography, when the sample is a gas, a difference of e.g. 3° C. between the temperature of the calibration gas in the sample chamber during calibration and the temperature of the sample gas in the sample chamber during a subsequent analysis will result in a 1% error in the sample results (based on the ideal gas law $PV = nRT$).

In one embodiment the injector is part of a multilayered microvalve assembly which includes a layer micromachined from a silicon wafer. A heater is integrated with one of the layers of the micro-valve assembly. This resistive trace heater and associated resistive trace temperature sensor are deposited on the surface of one of the layers for thermostatically-controlled heating of the microvalve assembly and the sample chamber.

DETAILED DESCRIPTION OF THE INVENTION

Figure 1A:
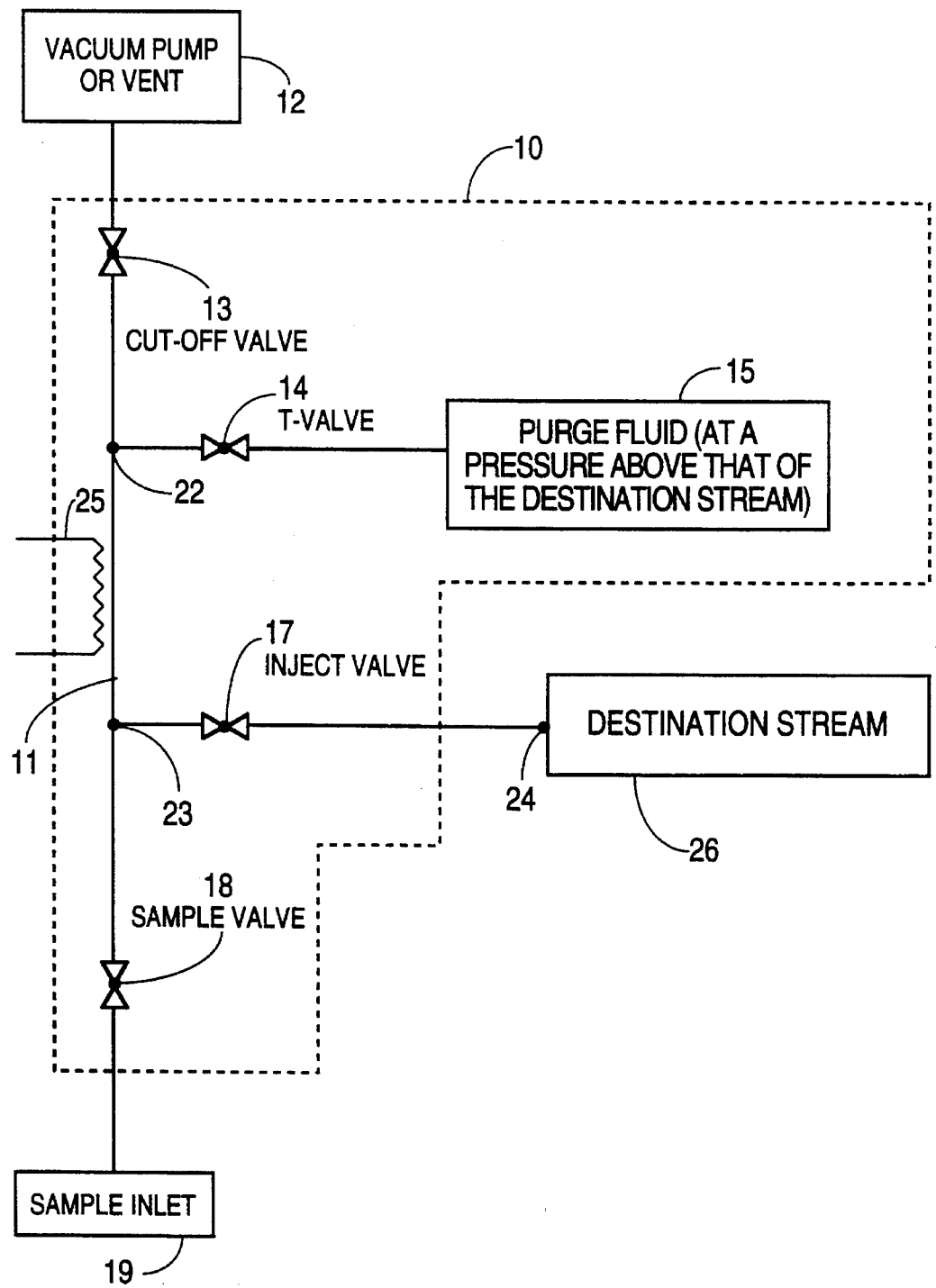
FIG. 1A is a schematic diagram of a fluid sample injector device in one embodiment of the present invention.

FIG. 1A is a schematic view of a fluid sample injector device in one embodiment of the present invention. The sample injector 10 (enclosed by a dotted line) includes a sample chamber 11 which is sealable by two valves 13 and 18 located respectively at each end of the sample chamber 11. The sample valve 18 controls the fluid sample entering sample chamber 11 from a sample inlet 19, and the cut-off valve 13 controls the communication of the sample chamber 11 to a vacuum pump or vent 12. The fluid sample enters the injector at the sample inlet 19, and flows under pressure (or is drawn in by a vacuum) through the sample chamber 11 to the conventional vacuum pump or vent 12. Additionally, the fluid pressure at the vent can be controlled or be open to the atmosphere.

After filling the sample chamber 11 with fluid sample, sample valve 18 is closed and the fluid sample is allowed to attain a reproducible temperature and pressure so that the amount of fluid sample in the fixed-volume portion of the chamber is reproduced. Then the cut-off valve 13 is closed, thereby trapping the fluid sample in the sample chamber. The time between the closure of the sample valve 18 and the closure of the cut-off valve 13 is called the "dwell time" (The optimal dwell time for the particular embodiment is determined experimentally). The T-valve 14 is opened, whereby purge fluid 15 at a pressure greater than the pressure of the destination stream 26 flows into the sample chamber at 22. The inject valve 17 is then opened and the fluid sample trapped in the sample chamber between valves 14 and 17 flows through the inject valve 17 into the destination stream 26. The part of the sample chamber between the T-valve 14 orifice and the inject valve 17 orifice is the "fixed-volume" portion of the sample chamber. The purge fluid entering the sample chamber at 22 forms a "fluid-lock" that segregates the sample in the sample chamber into two parts: the fixed-volume part which flows into the destination stream, and the remainder which does not flow into the destination stream.

When purge fluid emitted by the T-valve 14 has purged fluid sample from the fixed-volume portion of the sample chamber 11 into the destination stream 26, the inject valve 17 and then the T-valve 14 are closed. In another embodiment, the inject valve 17 and the T-valve 14 are opened and closed at the same time. Thus, in this embodiment the two valves 14 and 17 are operated with the same control signal, simplifying control. There is a wide range of suitable destination streams. For example: an open vessel (empty or containing some material or item); a pipe containing a fluid (gas or liquid), where the injected fluid sample enters the pipe through an appropriate fitting; a pipe containing a slurry or fluidized solid material.

The purge fluid can be any appropriate fluid for the particular embodiment. Desirable purge fluid properties may include: "inert" relative to the fluid sample, "inert" relative to the destination stream, inexpensive, readily available, easily utilized in the particular embodiment. The purge fluid source 15 is connected to T-valve 14 through a pressure regulator (not shown) which provides a stable regulated purge fluid supply at a pressure above that of the destination stream.

The performance of the injector 10 is improved by minimizing the internal volumes between 22 and 14, between 23 and 17, and between 17 and 24. Fluid sample is not drawn through 22 and 14, or 23 and 17 during the filling of the sample chamber with fluid sample. Therefore, in order to assure that fresh fluid sample fills these "unswept" or "dead" internal volumes, which are part of the fixed-volume portion of the sample chamber, these internal volumes should be as small as possible. In order to assure that the fluid sample is injected as a discrete "plug", the internal volume between 17 and 24 should be as low as possible, since the destination stream does not flow through this channel. Minimizing of the internal volume between 22 and 13, and between 23 and 18 is also advised, to facilitate injector miniaturization, to allow higher speeds of operation, to minimize the amount of sample required per injection, or other reasons. Valve 14 is preferably a T-valve to minimize the internal volume between 22 and 14. The through-channel of the T-valve is connected to the sample chamber 11 passage and forms a part of the sample chamber 11, while the branched channel of the T-valve is connected to the purge fluid source 15. When the T-valve 14 is opened, the purge fluid flows from the branched channel of the T-valve 14 into the through channel of the T-valve and typically spreads both ways (towards 13 and 23).

Figure 1B:
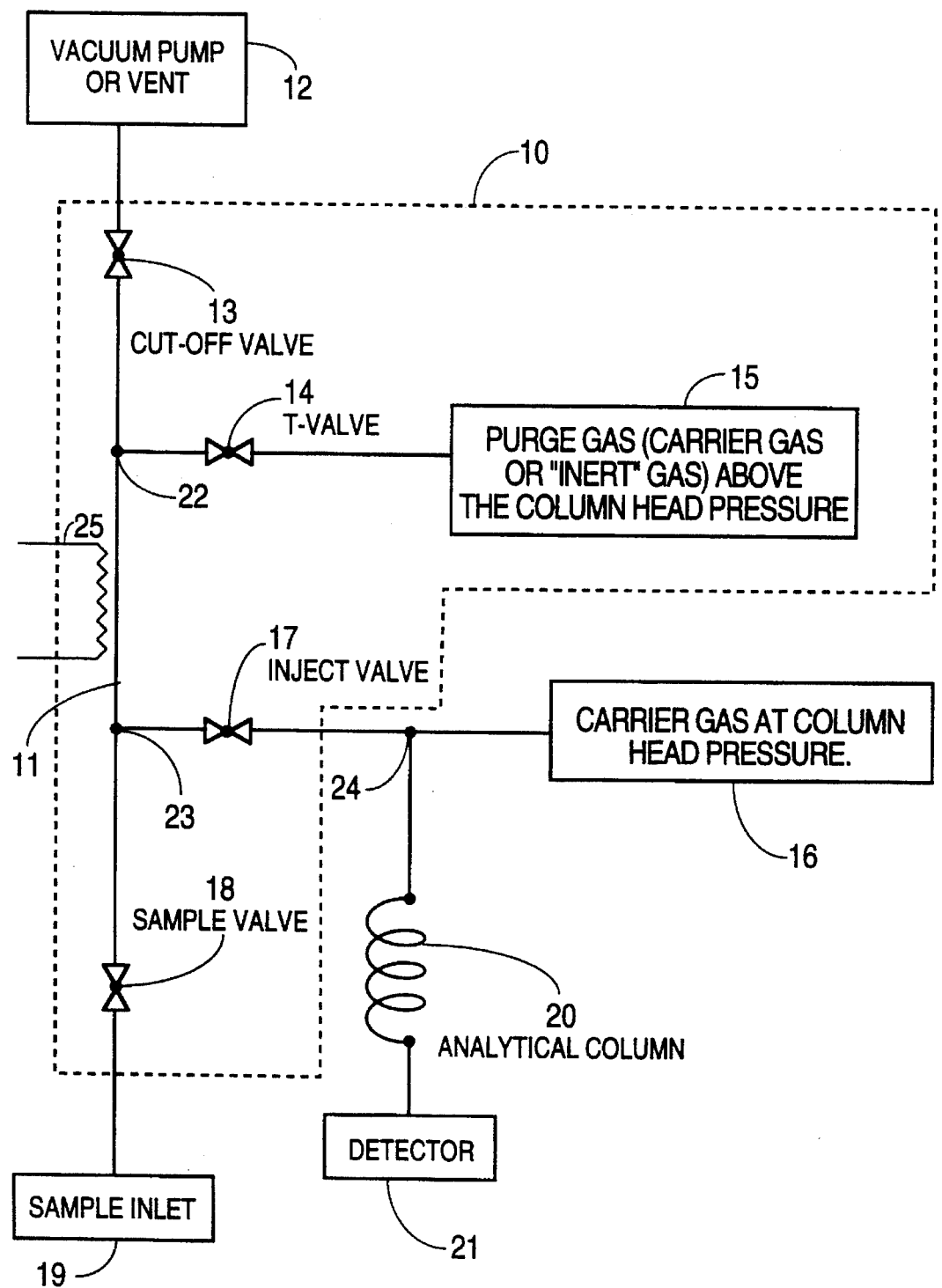
FIG. 1B is a schematic diagram of a gas chromatograph system including the injector device shown in FIG. 1A.

FIG. 1B is a schematic view of a gas chromatograph system which includes a fluid sample injector device shown in FIG. 1A. Like components in both figures are designated by the same reference numerals. Inject valve 17 is connected to a analytical column 20 where conventionally the individual components of the sample gas separate physically and are sensed by the detector 21 as they exit the analytical column 20. A carrier gas source 16 at a predetermined pressure (referred to as column head pressure) provides a carrier gas stream through the analytical column which is the "destination stream" referred to above. When the T-valve 14 and the inject valve 17 are open, the sample gas trapped in the sample chamber between valves 14 and 17 flows through the inject valve 17 into the carrier gas stream to the analytical column 20.

Figure 2A:
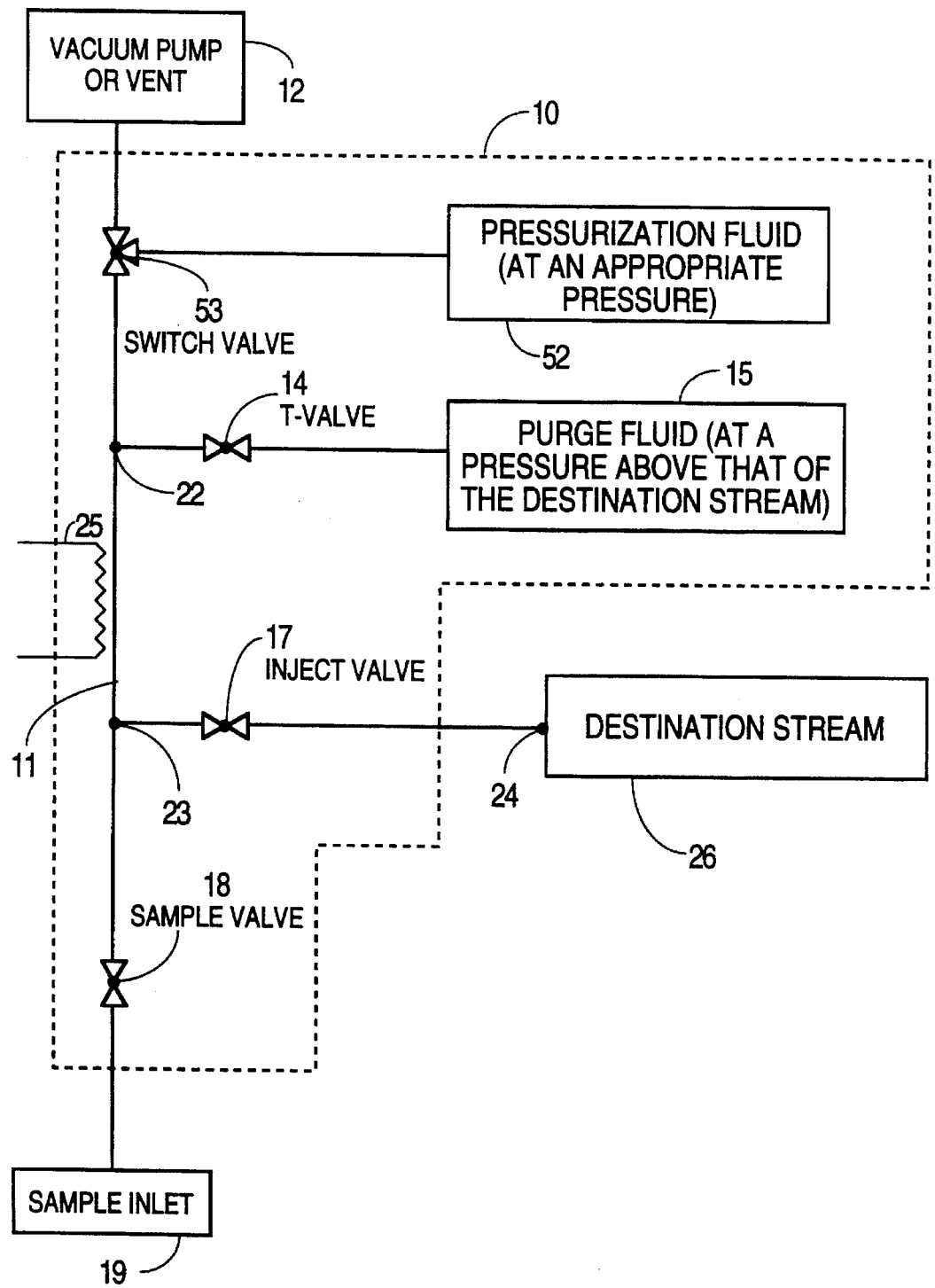
FIG. 2A is a schematic diagram of a fluid sample injector device in another embodiment of the present invention.

FIG. 2A is a schematic view of a fluid sample injector in accordance with another embodiment of the present invention. In this embodiment, the injector device 10 is similar to that of FIG. 1A except that the sample chamber 11 is sealed at one end by a valve 18, and at the other end by the application of pressure. This embodiment has the additions of a source of pressurization fluid 52 (which can be purge fluid, fluid sample or another appropriate fluid), and a switch valve 53 which toggles between connecting the sample chamber to the pressurization fluid source 52 and the vacuum pump or vent 12. The sample chamber 11 is essentially the space filled with fluid sample between the sample valve 18 and the switch valve 53. The fluid sample enters the injector at the sample inlet 19 and flows under pressure (or is drawn in by vacuum) through the sample chamber 11 to vacuum pump or vent 12. Additionally, the fluid pressure at the vent can be controlled or be open to the atmosphere.

After filling the sample chamber 11 with fluid sample, the sample valve 18 is closed. After some delay, called the "dwell time", the switch valve 53 is actuated to connect the sample chamber 11 to the pressurization fluid source 52 thereby trapping the fluid sample in the sample chamber 11 and pressurizing the fluid sample to the pressure of the pressurization fluid 52 for a certain amount of time, called the "pressurization time". The pressure of the pressurization fluid must be sufficient to cause the fluid sample in the fixed-volume portion of the sample chamber to flow effectively through the inject valve 17 during sample injection. A pressurization fluid pressure about equal to the pressure of the destination stream is adequate for one embodiment. The fluid sample in the sample chamber is allowed to attain a reproducible temperature and pressure before the sample injection event. The remainder of the procedure is the same as that described above reference with FIG. 1A.

The fluid sample may be pressurized and hence flow under its own pressure, or may be drawn in using vacuum pump 12, from the sample inlet 19 through the sample chamber 11. After fluid sample fills the sample chamber, a certain dwell time and a certain pressurization time are needed to allow the fluid sample to attain an appropriate temperature and pressure for the effective operation of the injector. For example, if a gaseous sample is in introduced into the sample chamber under its own pressure, then dwell time may be needed for excess sample gas to vent out of the sample chamber through the vacuum pump or vent 12. The dwell time depends on particular dimensions of the sample chamber and the pressures used, and other details specific to the particular embodiment (including the properties of the fluid sample and the destination stream).

The pressurization time in the FIG. 2A embodiment also depends on the particular chamber and channel structure, and the pressures used. There is an optimal pressurization time and an optimal dwell time, or a range of times for each particular embodiment of the invention, which can be obtained experimentally. The times are determined experimentally which produce the most reproducible sample injection volume over the range of operation variables relevant to the particular embodiment (for example, variation in sample inlet pressure).

The pressurization fluid can be any appropriate fluid for the particular embodiment. Desirable pressurization fluid properties may include: "inert" relative to the fluid sample, "inert" relative to the destination stream, inexpensive, readily available, easily utilized in the particular embodiment.

The pressurization fluid source 52 is connected to switch valve 53 through a pressure regulator (not shown) which provides a stable regulated pressurization fluid supply at an appropriate pressure. As was described above for the embodiment shown in FIG. 1A, the performance of the injector 10 shown in FIG. 2A is improved by minimizing the internal volumes between 22 and 14, between 23 and 17, and between 17 and 24; minimizing of the internal volume between 22 and 53, and between 23 and 18 is also similarly advantageous.

Figure 2B:
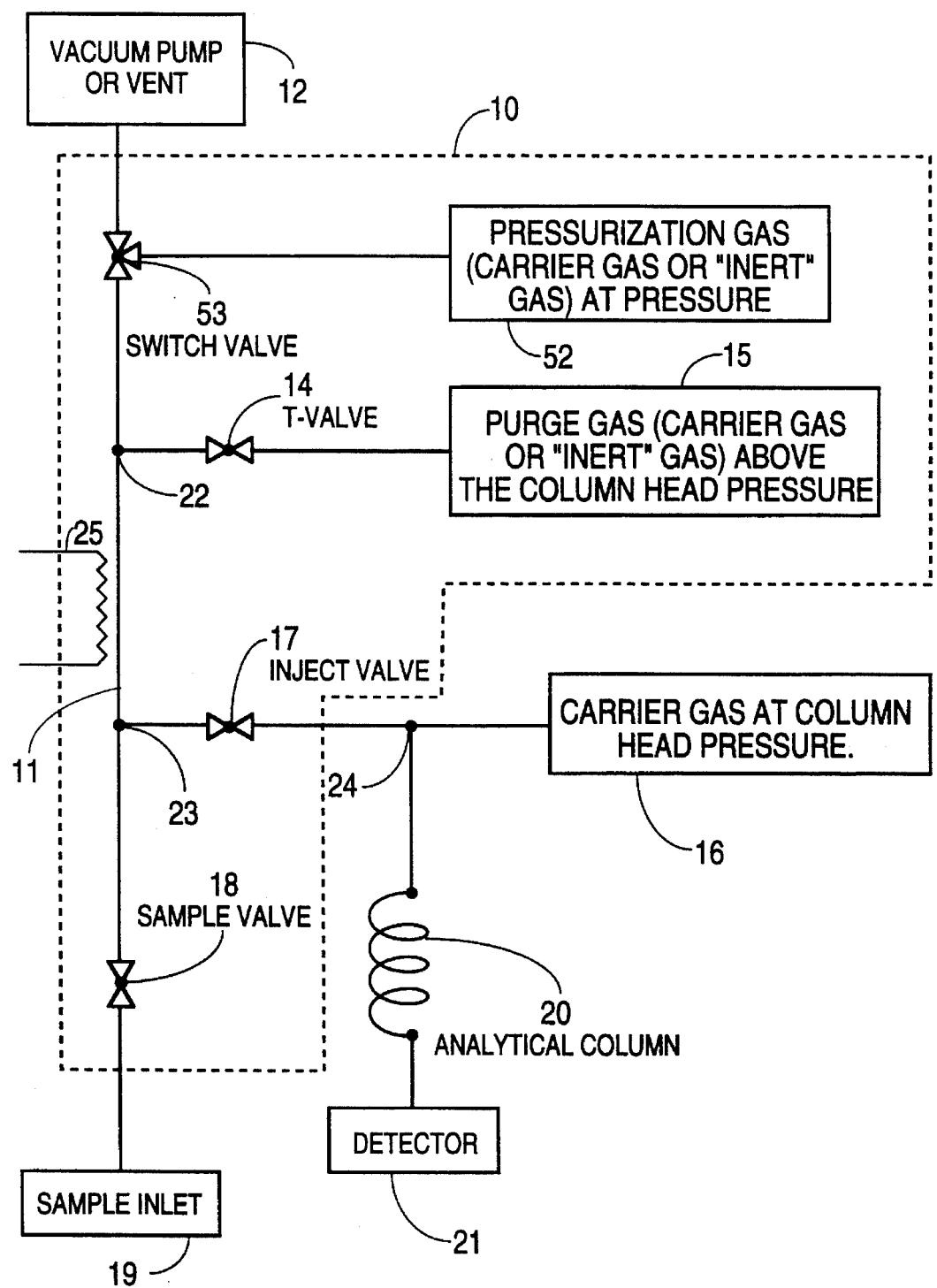
FIG. 2B is a schematic diagram of a gas chromatograph system including the injector device shown in FIG. 2A.

FIG. 2B is a schematic view of a gas chromatograph system with an injector device shown in FIG. 2A. The same reference numerals are designated for similar components as used in FIGS. 1A, 1B and 2A. The sample filling procedures in FIG. 2B are similar to those of FIG. 2A, and the sample injection procedures are similar to those in FIG. 1B.

For some embodiments, the destination stream, purge fluid and pressurization fluid flows can be linked and switched in various combinations while producing a fixed-volume injection at some point during the sequence of switching and linking the flows. For example, in a gas chromatograph, the carrier gas flow could be redirected: e.g. disconnected from the analytical column and passed through pressure and flow controllers if necessary and utilized as the source of purge gas or pressurization gas and carrier gas.

For micromachined-from-silicon-wafer versions of the two embodiments shown in FIGS. 1A and 2A, the valves are preferably diaphragm valves. When the diaphragm of the valve is subject to pressure, the diaphragm valve closes. When the pressure applied to the diaphragm is released, the valve opens. The control pressure applied to the diaphragm of the valves is much higher than that of the fluid stream being controlled, in order for the valve diaphragm to seal adequately against the pressure of the fluid stream being controlled.

Figure 3A:
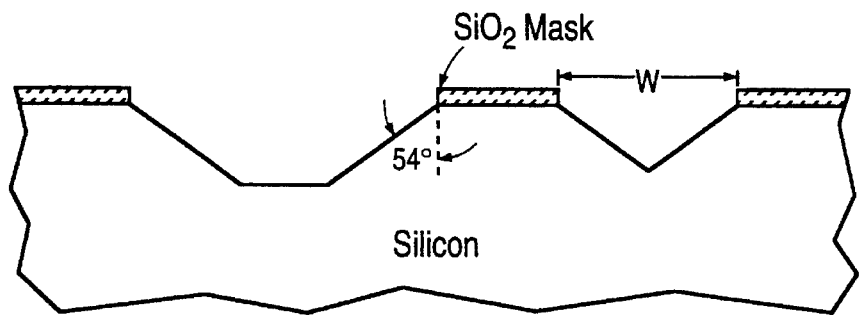
FIGS. 3A–3C show cross sections of grooves etched in silicon with respectively KOH etchant in (100) silicon, KOH in (110) silicon, and HF—HNO$_3$ etchant.
Figure 3B:
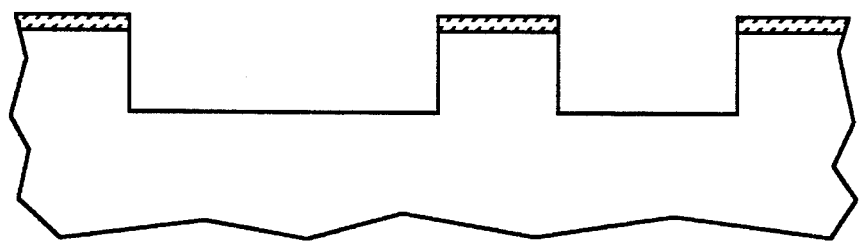
Figure 3C:
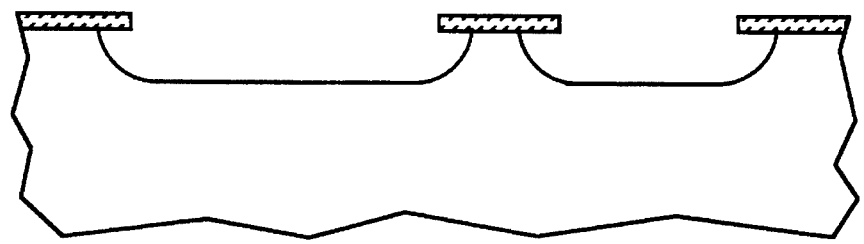

The conventional process for micromachining a silicon wafer to form injector 10 includes a series of oxidation, photolithography, and etching steps similar to well known integrated circuit device processing. Through the use of isotropic and anisotropic silicon etches, very small-volume holes, shallow wells and grooves which form the miniature valves and capillary channels are precisely fabricated on a silicon wafer. Several groove cross-sectional profiles are available, depending upon the crystallographic orientation of the silicon, the etchant used, etc. An anisotropic etchant such as potassium hydroxide (KOH) results in a V-groove profile in (100) oriented silicon as shown in FIG. 3A. The sides of the "V" are determined by crystallographic planes in the silicon, and for a narrow groove in which the V walls meet, the depth of the groove can be precisely controlled by the width W of the opening in the oxide etch mask. In (110) oriented silicon or along certain crystallographic directions in (100) silicon, KOH etches grooves with a perfectly vertical wall as shown in FIG. 3B. A disadvantage of the anisotropic etch etches, however is that the desired groove profiles are achieved only if the grooves lie along specific crystallographic axes, and certain shapes such as square corners and circles cannot be realized. A mixture of hydrofluoric and nitric acids (HF—HNO$_3$) can be used as an isotropic silicon etchant to produce the grooves shown in FIG. 3C. This produces approximately rectangular grooves, oriented in any direction on the wafer as well as valve seats.

Figure 4:
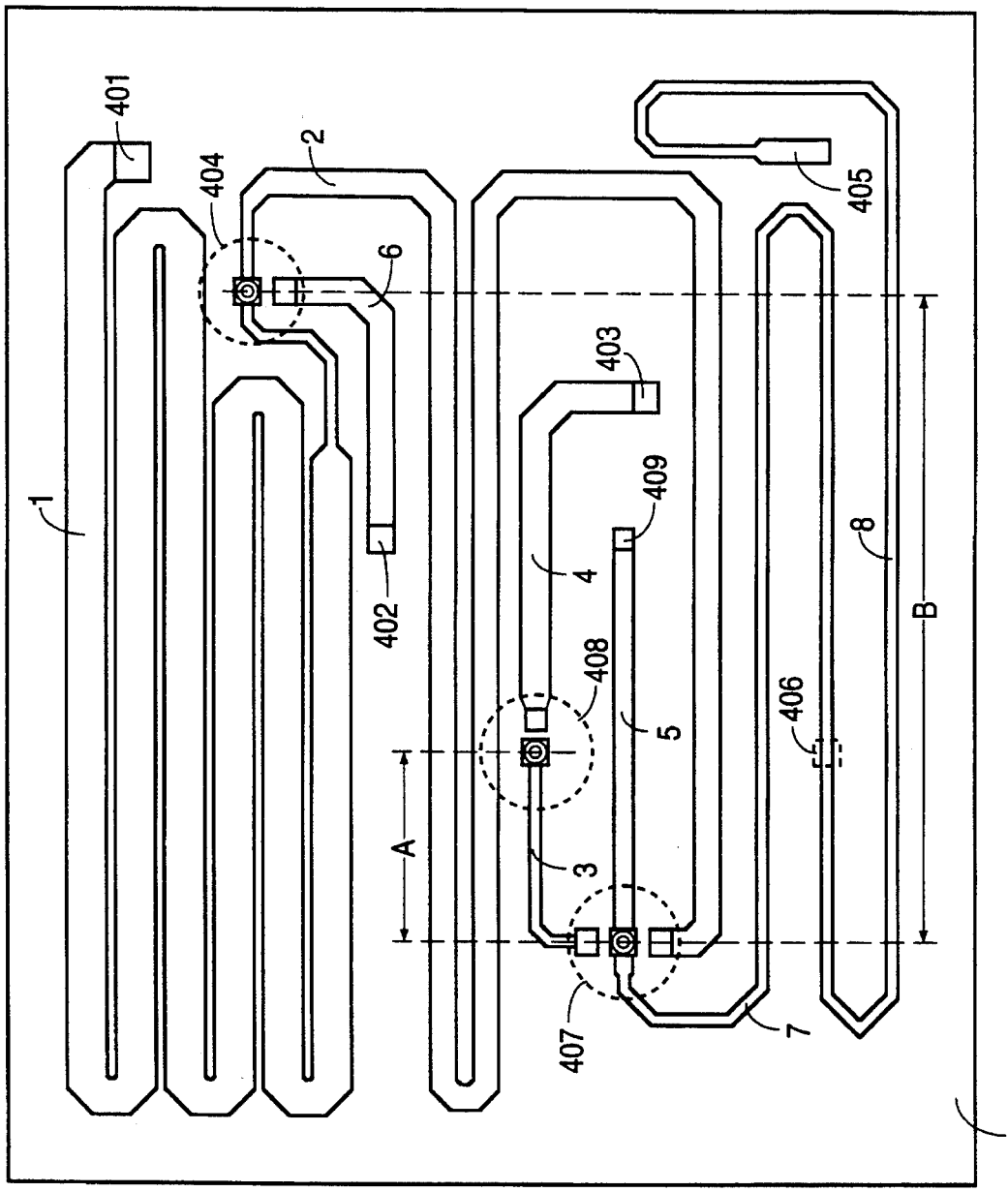
FIG. 4 shows a micromachined injector formed on a silicon wafer.
Figure 5A:
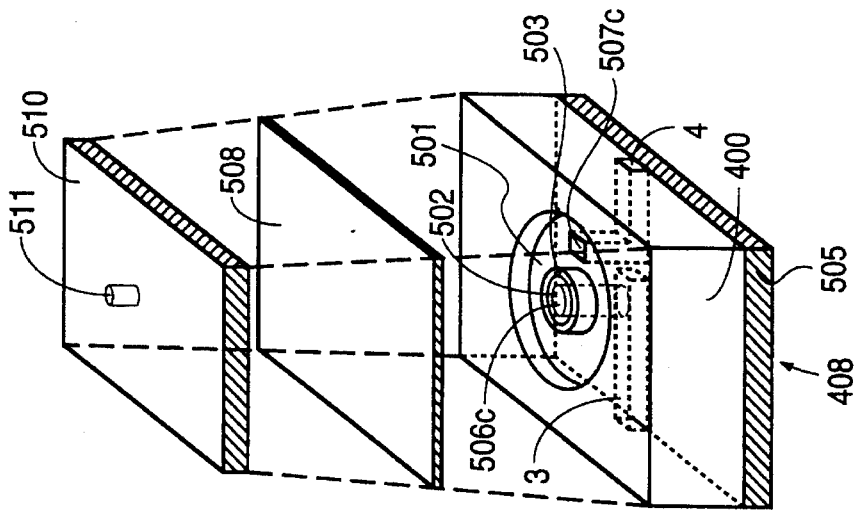
FIGS. 5A–5C are perspective views showing the structure of the microvalves in FIG. 4.
Figure 5B:
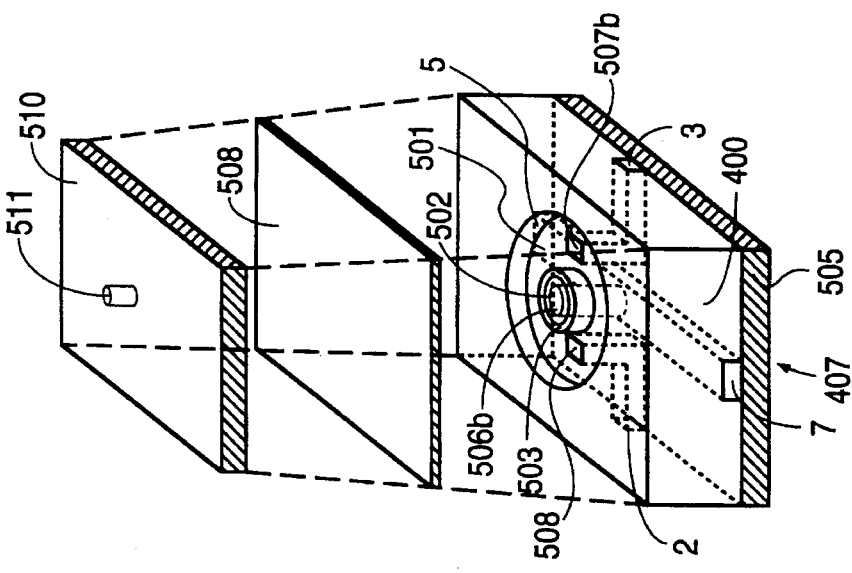
Figure 5C:
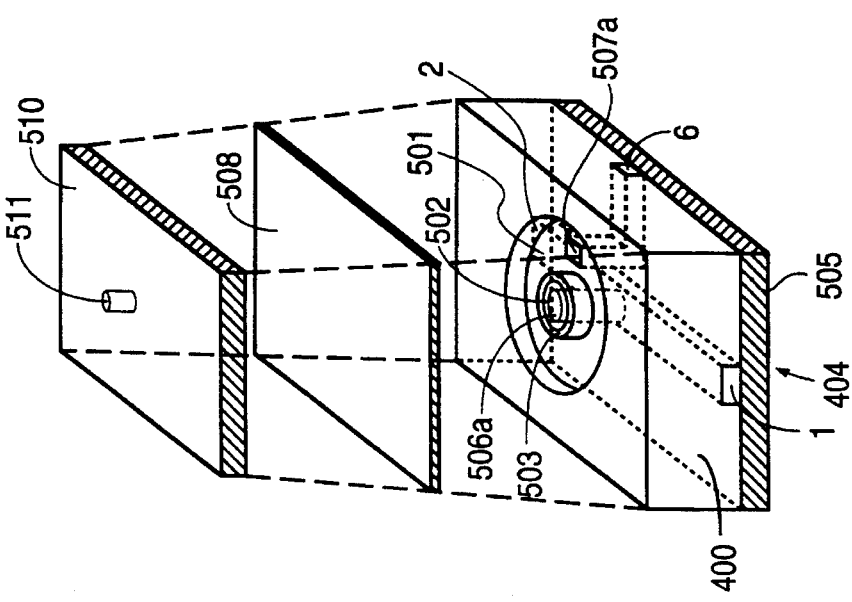

FIG. 4 shows a plan view of a silicon wafer for one embodiment of the injector device of the present invention which has gas channels and valve seats formed by employing conventional silicon micromachining and packaging technology. FIG. 4 is one embodiment of the structure shown in FIGS. 2A and 2B. Further construction details are provided in above-referenced U.S. Pat. No. 4,474,889. To form one embodiment of the injector device of the present invention, the wafer 400 is sandwiched between several other layers, which are not shown in FIG. 4 (but all the layers are shown in FIGS. 5A, 5B and 5C described in detail below). A plate 505 (in FIGS. 5A, 5B and 5C) is bonded to wafer 400 to seal the etched grooves in wafer 400, thereby forming microchannels. A flexible material 508 (in FIGS. 5A, 5B and 5C) which acts as the flexible diaphragm of the valves 408, 407, and 404 is bonded to the other side of wafer 400 (the "valve seat side"). Another plate 510 (in FIGS. 5A, 5B, and 5C) is bonded to the flexible material layer. The "sandwich" thus formed consists of four layers: plate layer 505, silicon wafer 400 layer, flexible material layer 508, plate layer 510. In one embodiment, pyrex glass is used for the plates 505 and 510, and the flexible material is a Dupont product called Kapton (a sheet material comprised of three layers: Teflon, polyimide, Teflon). The pyrex plate on the microchannel side of wafer 400 is bonded to wafer 400 using anodic bonding. The Kapton and the other pyrex plate are then attached by pressing and heating the assembled layers. The Kapton becomes sticky when heated, thereby bonding to wafer 400 and the pyrex plate. Conduction of gases into and out of the injector assembly is through holes in the pyrex plates. Tubes for conducting the gases outside the injector assembly are bonded in the holes in the pyrex plates (stainless steel tubes are used in one embodiment). The tubes are bonded to the pyrex plate using UV-curing adhesive in one embodiment. Other adhesives can be used for bonding, or the tubes can be soldered to the plates.

As shown in FIG. 4, three valve seats (sample valve 408, inject valve 407 and T-valve and 404) and channels 1– 8 are conventionally formed on a silicon wafer 400. Valves 408, 407, and 404 correspond to valves 18, 17, and 14 respectively in FIGS. 1A, 1B and 2A, 2B. A carrier gas source 16 (not shown in FIG. 4) is connected at a port 406 to provide the injector with carrier gas. The analytical column 20 is connected to channel 5 through port 409. A reference carrier gas stream exits the injector at port 405. (If a reference carrier gas stream is not required, then port 405 and channel 8 are not required.) Channels 1, 2, and 3, and the tubing and conduits (not shown in FIG. 4) which connect port 401 to the switch valve 53 (not shown in FIG. 4) comprise the sample chamber similar to sample chamber 11 in FIGS. 2A and 2B. Channel 2 and the annular space between the valve 407 diaphragm and silicon wafer 400 form the fixed-volume portion of the sample chamber and define the sample volume to be injected at the orifice of the inject valve 407 into the carrier gas stream which flows through channel 5 to the analytical column (not shown). This orifice corresponds to junction 24 in FIGS. 1A, 1B and FIGS. 2A, 2B. A tube conducts carrier gas from the carrier gas source 16 to port 406 on wafer 400, channels 7 and 5 conduct carrier gas in wafer 400 between inlet port 406 and outlet port 409, and a tube conducts carrier gas from port 409 to the analytical column (These conduits correspond to the carrier gas conduits between the carrier gas supply 16 to the analytical column 20 in FIG. 1B and FIG. 2B).

In one embodiment using the silicon wafer in FIG. 4, the carrier gas source 16 is used also as the pressurization gas source 52. The purge gas source 15 is also carrier gas, but at a pressure about 13 psi above the pressure of the carrier gas source 16.

An injector purge sequence may required to purge air from the purge gas source 15, the tubing that conducts purge gas to port 402, channel 6, and the T-valve 404. For example, open T-valve 404 and allow purge gas to flow from the purge gas source through the T-valve 404 and out the vacuum pump or vent 12, so that residual air in those chambers is purged. During manufacturing and out-of-service episodes, air may migrate into these chambers.

In order to make one FIG. 1B version in a micromachined-from-silicon format like that of FIG. 4, a cut-off valve 13 is added to wafer 400 near port 401, and port 401 is connected directly to the vacuum pump or vent 12 (a switch valve 53 is not used).

FIGS. 5A–5C are the perspective views showing the structures respectively of the microvalves 404, 407 and 408. Each of the three valve seats includes an annular recess 501, a central recess 502, and an annular ridge 503 between recesses 501 and 502, a flexible diaphragm layer material 508 pressed against the valve seat side of wafer 400, a plate 505 bonded on the microchannel side of the wafer 400 to seal the grooves or channels, and a plate 510 pressed against the flexible diaphragm layer, material 508. The control pressure which controls the flexible diaphragm to open and close the valve communicates with the flexible diaphragm through port 511 on plate 510. An orifice is formed in the center of the central recess 502 communicating to a channel or channels formed on the microchannel side. At least one through hole is formed in the annular recess 501 communicating to a channel etched on the microchannel side of the wafer 400. When pressure is applied through port 511, the diaphragm seats against the annular ridge 503 sealing the orifice. When the pressure is released, gas flows through the orifice between the channels connected to the orifice and the channels connected to the through hole in the recess 501.

For the T-valve 404 in FIG. 5A, channel 1 connects to channel 2 at the valve orifice on the microchannel side of wafer 400. Hole 507a couples to a purge gas source via channel 6. When the T-valve 404 is opened, the purge gas flows from the hole 507a into the orifice 506a and spreads typically both ways along the channel 1 and 2 in the form of a "T". Therefore, a valve with such a valve seat is called herein a T-valve. The sample valve 408 in FIG. 5C has an orifice 506c communicating to a channel 3 on the microchannel side of the wafer 400, and a hole 507c communicating to a channel 4. During sample chamber filling, when the sample valve 408 opens, sample gas flows from the through hole 507c to the valve orifice 506c. The inject valve 407 in FIG. 5B has an orifice 506b communicating to a channel 5 and two through holes 507b and 508 communicating to the channel 3 and channel 2 respectively. Through holes 507b and 508 communicate through the annular space between the valve diaphragm and wafer 400, whether the valve is open or closed. When the inject valve opens, sample gas flows from through hole 508, through the valve orifice 506b, into channel 5. Carrier gas is always able to flow freely through channel 7 to channel 5 at the orifice of inject valve 407, except for a brief interruption during sample injection.

In one embodiment of the present invention, the diaphragm of each microvalve is pressurized with helium gas, e.g., to close the valves. When the helium pressure is released, the diaphragm relaxes to open the valves. The helium gas pressure applied to the diaphragm of each microvalve is controlled by associated conventional electrically-controlled solenoids valves (not shown). As mentioned before, in one embodiment valves 404 and 407 are controlled by the same solenoid since they are opened and closed at the same time. The helium gas pressure used to control the diaphragm valves is about 80 to 100 psig. A sample gas source is connected to channel 4 at an inlet port 403. A carrier gas source 16 is connected to the channels 7 and 8 at an inlet port 406 and provides a stable regulated head pressure of carrier gas entering the inlet port 406. The carrier gas pressure is about 20 psig at port 406 in one embodiment of the present invention. Channel 8 between ports 406 and 405, and channel 7 between port 406 and the orifice of inject valve 407, restrict the flows of carrier gas and provide some regulation of the flows. The purge gas source 15 (not shown in FIG. 4) is connected at an inlet port 402 via a pressure regulator, which provides a stable regulated pressure of purge gas. In one embodiment, the purge gas is carrier gas entering the inlet port 402 at about 13 psi above the carrier gas pressure at the carrier gas source 16.

The sample gas may be pressurized and hence will flow under its own pressure, or may be drawn in using a vacuum pump connected to the port 401 from the port 403 to port 401 through channel 4, sample valve 408, channel 3, through holes 507b and 508 in inject valve 407, channel 2 and channel 1. After sample gas fills the sample chamber a certain amount of time is needed to wait for the sample to equilibrate, about 140 milliseconds in one embodiment (the dwell time). Then the sample gas in the sample chamber is pressurized for a certain amount of time (the pressurization time) by using the same pressure-regulated carrier gas source 16 that supplies carrier gas at port 406. The pressurization time in one embodiment is about 210 milliseconds. After pressurization, the T-valve 404 and inject valve 407 are opened and carrier gas at a pressure about 13 psi higher than the column head pressure passes through the orifice 506a and enters the channel 2 as well as channel 1 to inject the sample gas in the channel 2 into the analytical column via the opened inject valve 407 and channel 5. The volume of the whole channel 2 from the orifice of the T-valve 404 to the orifice of the inject valve 407, including the annular space between the inject valve diaphragm and the silicon wafer, contains the fixed-volume to be injected into the analytical column.

For the embodiment shown in FIG. 4, the channel 8 functions to deliver a reference carrier gas stream to a particular design thermal conductivity detector (shown schematically in FIG. 1B and FIG. 2B as detector 21). For embodiments that do not require a reference carrier gas stream, the channel 8 and port 405 are not required.

The approximate dimensions of the features in one micromachined-in-silicon embodiment are as follows. Wafer 400 has a size of 19 mm by 25 mm, and a thickness of 0.30 mm. Valve seats 404, 407 and 408 have a 2.5 mm diameter. The widths for channels 1–6 are 1 mm, 0.4 mm, 0.1 mm, 1 mm, 0.2 mm and 0.4 mm respectively. The depths thereof are 0.06 mm. The cross-sectional shape is rectangular. The volume of channel 2 is approximately 2 microliters. The fixed-volume to be injected is directly related to the volume of channel 2. The fixed-volume injected can be varied by changing the length, width or depth of channel 2. The channels 7 and 8 have a V-shape cross-section, with a depth of 0.04 mm and a top opening of 0.08 mm. The distances between valves 407 and 408 and between valves 407 and 404, designated in FIG. 4 as A and B are 3.5 mm and 15 mm respectively. The diameter of the tubes are 0.50 mm to 0.70 mm, with 0.13 mm wall thickness. The pyrex plates are 1.3 mm thick. The Dupont Kapton flexible membrane is 0.07 mm thick (0.01 mm Teflon, 0.050 mm polyimide, 0.01 mm Teflon).

As mentioned previously, reproducing the temperature of the sample gas in the chamber is desirable for high accuracy analyses, since the number of moles of gas in the sample chamber varies inversely with the temperature of the gas (absolute temperature).

A heater 25 (FIGS. 1A, 1B and 2A, 2B) heats the sample gas in the sample chamber 11 to a predetermined temperature in one embodiment. The accurate, reproducible temperature and pressure of the sample gas in the chamber 11 ensure an accurate number of moles of sample gas injected into the analytical column, providing high accuracy analyses.

The heater in one embodiment is integrated with the injector structure to heat and thermostatically control the injector device. In one embodiment a resistive metal (nickel) trace about 7,500 Å thick and about 45 mils wide and having a resistance of about 20 ohms is deposited on the surface of the (pyrex glass) plate 510 of the injector overlying the valve diaphragm material, and a controlled electrical current passes through the trace to heat the injector. The nickel trace is deposited on chromium layer about 50 Å thick. Another similar but narrower resistive metal trace (nickel, about 5 mils wide) is adjacent to the heater trace. By sensing the resistance of the adjacent trace, the temperature of the injector can be estimated and controlled by well known methods. The resistive metal heater trace is hence conventionally controlled to maintain a constant temperature. Additionally, the sample inlet tube and the inlet port (not shown) to the injector device 10 and the outlet port can be heated to a controlled temperature by separately controlled resistive heating.

The inlet tube in one embodiment is heated resistively by direct application of electric current to the e.g. thin walled metal tube. The inlet port in one embodiment is heated by a coil of resistive wire wrapped around it. Additional details of this heating are in copending and commonly owned application Ser. No. 08/159,185 entitled "Heated-Zone Gas Chromatograph", invented by Alan D. Loux, R. Sjhon Minners, and Paul H. Johnson, attorney docket No. M-2535, incorporated by reference.

Although the present invention has been described and illustrated with particular embodiments, it is clearly understood that this is by way of illustration and example only and is not to be taken by way of limitation. Different modifications, variations and improvements can be made without departing from the spirit and scope of the invention. The present invention is not limited in use to gas chromatography; it can be used for an injector to inject a fluid into other streams, for example, to inject a small quantity of a drug into an intravenous stream for intravenous transfusion. The spirit and scope of the present invention is limited only by the appended claims.

What is claimed is:

1. An injector assembly for injecting a fixed volume of a first fluid comprising:
   a chamber for containing an amount of the first fluid, and having a first valve at one end to connect said chamber to a first fluid source, a portion of the chamber defining said fixed volume;
   a second valve connected to the chamber at one end of the fixed-volume portion, thereby causing a second fluid stream from a second fluid source to flow into the fixed-volume portion and forcing the first fluid in the fixed-volume portion into a destination passage;
   a third valve connected to the chamber at an end of the fixed-volume portion opposite said second valve, and communicating the fixed-volume portion to the destination passage; and
   a fourth valve connected to the chamber at an end opposite said first valve, thereby trapping the first fluid in the chamber.

2. An injector assembly as in claim 1, wherein said first fluid source has a first pressure, said second fluid source has a second pressure and said destination passage communicates with a destination stream.

3. An injector assembly as in claim 1, wherein said second valve is a T-valve, a through channel of which is connected to the chamber and forms a part thereof, and a branched channel of which is connected to the second fluid source.

4. An injector assembly as in claim 1, further comprising a heater in thermal contact with the fixed-volume portion of the chamber, thereby heating the first fluid trapped in the fixed-volume portion of the chamber to a predetermined temperature.

5. An injector assembly for injecting a fixed volume of a first fluid comprising:
   a chamber for containing an amount of the first fluid, and having a first valve at one end to connect said chamber to a first fluid source, a portion of the chamber defining said fixed volume;
   a second valve connected to the chamber at one end of the fixed-volume portion, thereby causing a second fluid stream from a second fluid source to flow into the fixed-volume portion and forcing the first fluid in the fixed-volume portion into a destination passage;
   a third valve connected to the chamber at an end of the fixed-volume portion opposite said second valve, and communicating the fixed-volume portion to the destination passage;
   wherein an end of the chamber opposite said first valve is adapted to connect to a pressure source for trapping the first fluid in the chamber.

6. An injector assembly as in claim 5, wherein said first fluid source has a first pressure, said second fluid source has a second pressure and said destination passage communicates with a destination stream.

7. An injector assembly as in claim 5, additionally comprising a fourth valve between the end of the chamber opposite said first valve and the pressure source.

8. An injector assembly as in claim 5, wherein said second valve is a T-valve, a through channel of which is connected to the chamber and forms a part thereof, and a branched channel of which is connected to the second fluid source.

9. An injector assembly as in claim 5, further comprising a heater in thermal contact with the fixed-volume portion of the chamber, thereby heating the first fluid trapped in the fixed-volume portion of the chamber to a predetermined temperature.

10. An injector device for injecting a fixed volume of a first fluid into a destination stream composing:
    a wafer-like substrate;
    a first fluid groove formed in the substrate for containing the first fluid, a section of the first fluid groove defining said fixed volume;
    a first valve, a seat of which is formed in the substrate, thereby passing the first fluid from a first fluid source therethrough into the first fluid groove;
    a second valve, a seat of which is formed in the substrate, connected at one end of the fixed-volume section of the first fluid groove, thereby passing a second fluid into said fixed-volume section and forcing the first fluid in said fixed-volume section into a destination passage which communicates with the destination stream;
    a third valve, a seat of which is formed in the substrate; connected at an end of the fixed-volume section of the first fluid groove opposite said second valve, and communicating the fixed-volume section to the destination passage;
    a fourth valve connected to the first fluid groove at an end opposite said first valve, thereby trapping the first fluid therein;
    a first, inflexible layer overlying the portion of the substrate in which the first fluid groove is formed; and
    a second, flexible layer overlying the portion of the substrate in which the valve seats are formed, thereby serving as a diaphragm for each valve having a seat formed in the substrate.

11. An injector device as in claim 10, further comprising a heater in thermal contact with the fixed-volume portion of the first fluid groove, thereby heating the first fluid trapped in the fixed-volume portion of the first fluid groove to a predetermined temperature.

12. An injector device as in claim 10, wherein said second valve is a T-valve, a through channel of which is connected to the first fluid groove and forms a part thereof, and a branched channel of which is connected to a source of the second fluid.

13. An injector device as in claim 11 wherein a heater is incorporated in a layer in thermal contact with the fixed-volume portion of the first fluid groove, thereby heating the first fluid in the fixed-volume portion of the first fluid groove.

14. An injector device as in claim 11 wherein a first resistive trace is deposited on a surface of a layer in thermal contact with the fixed-volume portion of the first fluid groove, thereby conducting an electrical current to heat the first fluid in the fixed-volume portion of the first fluid groove.

15. An injector device as in claim 14 wherein a second resistive trace is deposited on a surface of a layer in thermal contact with the fixed-volume portion of the first fluid groove, thereby sensing indirectly the temperature of the fixed-volume portion of the first fluid in the first fluid groove.

16. A method for introducing a fixed volume of a sample fluid into a destination stream comprising the steps of:
    providing a chamber for containing the sample fluid, a portion of the chamber defining said fixed volume;

providing a first valve connected at one end of the fixed-volume portion to a purge fluid source;

providing a second valve connected at an end of the fixed-volume portion opposite the first valve to a destination passage which communicates with the destination stream;

closing the first and second valves;

introducing the sample fluid into the chamber;

trapping the sample fluid in the chamber;

pressurizing the sample fluid in the chamber to a reproducible pressure for a particular amount of time before opening the first and second valves; and opening the first and second valves to cause a purge fluid stream from the purge fluid source to pass the first valve and enter the fixed-volume portion of the chamber and force the sample fluid in the fixed-volume portion to pass the second valve to the destination passage which communicates with the destination stream.

17. A method as in claim 16 further comprising a step of heating the sample fluid in the fixed-volume portion of the chamber to a reproducible temperature before opening the first and second valves.

18. A method as in claim 16 wherein said first valve is a T-valve, a through channel of which is connected to the first fluid groove and forms a part thereof, and a branched channel of which is connected to the purge fluid source.

19. A method as in claim 16 further comprising prior to the introducing step, the step of executing a sequence of valve openings, thereby to purge undesirable fluids.

20. An injector device for injecting a fixed volume of a first fluid into a destination stream comprising:

a wafer-like substrate;

a first fluid groove formed in the substrate for containing the first fluid, a section of the first fluid groove defining said fixed volume;

a first valve, a seat of which is formed in the substrate, thereby passing the first fluid from a first fluid source therethrough into the first fluid groove;

a second valve, a seat of which is formed in the substrate, connected at one end of the fixed-volume section of the first fluid groove, thereby passing a second fluid into said fixed-volume section and forcing the first fluid in said fixed-volume section into a destination passage which communicates with the destination stream;

a third valve, a seat of which is formed in the substrate, connected at an end of the fixed-volume section of the first fluid groove, and communicating the fixed-volume section to the destination passage;

wherein an end of the first fluid groove opposite said first valve is adapted to connect to a pressure source, thereby trapping the first fluid in the first fluid groove;

a first, inflexible layer overlying the portion of the substrate in which the first fluid groove is formed; and a second, flexible layer overlying the portion of the substrate in which the valve seats are formed, thereby serving as a diaphragm for each valve having a seat formed in the substrate.

21. An injector device as in claim 20, further comprising a heater in thermal contact with the fixed-volume portion of the first fluid groove, thereby heating the first fluid trapped in the fixed-volume portion of the first fluid groove to a predetermined temperature.

22. An injector device as in claim 20, wherein said second valve is a T-valve, a through channel of which is connected to the first fluid groove and forms a part thereof, and a branched channel of which is connected to a source of the second fluid.

23. An injector device as in claim 20 wherein a heater is incorporated in a layer in thermal contact with the fixed-volume portion of the first fluid groove, thereby heating the first fluid in the fixed-volume portion of the first fluid groove.

24. An injector device as in claim 20 wherein a first resistive trace is deposited on a surface of a layer in thermal contact with the fixed-volume portion of the first fluid groove, thereby conducting an electrical current to heat the first fluid in the fixed-volume portion of the first fluid groove.

25. An injector device as in claim 24 wherein a second resistive trace is deposited on a surface of a layer in thermal contact with the fixed-volume portion of the first fluid groove, thereby sensing indirectly the temperature of the first fluid in the fixed-volume portion of the first fluid groove.

26. An injector assembly as in claim 20, additionally comprising a fourth valve between the end of the first fluid groove opposite said first valve and the pressure source.

27. A gas chromatograph system for analyzing a fixed volume of a first fluid, comprising:

a chamber for containing an amount of the first fluid, and having a first valve at one end to connect said chamber to a first fluid source, a portion of the chamber defining said fixed volume;

a second valve connected to the chamber at one end of the fixed-volume portion, thereby causing a second fluid stream from a second fluid source to flow into the fixed-volume portion and forcing any the first fluid in the fixed-volume portion into a destination passage;

a third valve connected to the chamber at an end of the fixed-volume portion opposite said second valve, and communicating the fixed-volume portion to the destination passage;

a fourth valve connected to the chamber at an end opposite said first valve, thereby trapping the first fluid in the chamber;

a third fluid source connected at an inlet to the destination passage, wherein a pressure of a third fluid stream from said third fluid source is less than a pressure of the second fluid stream;

an analytical column connected at an outlet of the destination passage; and a detector connected at an outlet of said analytical column.

28. A gas chromatograph system as in claim 27, additionally comprising a vacuum pump connected to said fourth valve thereby drawing the first fluid through the chamber.

29. A gas chromatograph system as in claim 27, additionally comprising a fourth fluid source connected to said fourth valve, thereby pressurizing the first fluid trapped in the chamber to a predetermined pressure.

30. A gas chromatograph system for analyzing a fixed volume of a first fluid, comprising:

a wafer-like substrate;

a first fluid groove formed in the substrate for containing the first fluid, a section of the first fluid groove defining said fixed volume;

a first valve, a seat of which is formed in the substrate, thereby passing the first fluid from a first fluid source therethrough into the first fluid groove;

a second valve, a seat of which is formed in the substrate, connected at one end of the fixed-volume section of the first fluid groove, thereby passing a second fluid into said fixed-volume section and forcing the first fluid in said fixed-volume section into a destination passage which communicates with the destination stream;

a third valve, a seat of which is formed in the substrate, connected at an end of the fixed-volume section of the first fluid groove opposite said second valve, and communicating the fixed-volume section to the destination passage;

a fourth valve connected to the first fluid groove at an end opposite said first valve, thereby trapping the first fluid therein;

a first, inflexible layer overlying the portion of the substrate in which the first fluid groove is formed;

a second, flexible layer overlying the portion of the substrate in which the valve seats are formed, thereby serving as a diaphragm for each valve having a seat formed in the substrate;

a third fluid source connected at an inlet to the destination passage, wherein a pressure of a third fluid stream from said third fluid source is less than a pressure of the second fluid stream;

an analytical column connected at an outlet of the destination passage; and a detector connected at an outlet of said analytical column.

31. A gas chromatograph system as in claim 30, additionally comprising a vacuum pump connected to said fourth valve, thereby drawing the first fluid through the first fluid groove.

32. A gas chromatograph system as in claim 30, additionally comprising a fourth fluid source connected to said fourth valve, thereby pressurizing the first fluid trapped in the first fluid groove to a predetermined pressure.

* * * * *